United States Patent [19]

Brenner et al.

[11] 4,340,600

[45] Jul. 20, 1982

[54] RENAL DILATING METHODS AND COMPOSITIONS USING 4-(3,4-DIHYDROXYPHENYL)-1,2,3,4-TETRAHYDROISOQUINOLINES

[75] Inventors: L. Martin Brenner, Havertown, Pa.; Joe R. Wardell, Jr., Voorhees Township, Camden County, N.J.

[73] Assignee: SmithKline Corporation, Philadelphia, Pa.

[21] Appl. No.: 152,252

[22] Filed: May 22, 1980

[51] Int. Cl.$^3$ .................... A61K 31/47; C07D 217/16
[52] U.S. Cl. .................................. 424/258; 546/143; 546/144
[58] Field of Search ................ 540/144, 143; 424/258

[56] References Cited

U.S. PATENT DOCUMENTS

| | | | |
|---|---|---|---|
| 3,577,424 | 5/1971 | Ehrhart et al. | 546/143 |
| 3,870,722 | 3/1975 | Houlihan et al. | 424/258 |
| 3,872,125 | 3/1975 | Houlihan et al. | 424/258 |
| 4,185,105 | 1/1980 | Schmitt et al. | 546/143 |

FOREIGN PATENT DOCUMENTS

| | | | |
|---|---|---|---|
| 698033 | 11/1967 | Belgium . | |
| 844783 | 1/1977 | Belgium . | |
| 15 | 12/1978 | European Pat. Off. . | |
| 11644192 | 9/1969 | United Kingdom | 546/143 |

OTHER PUBLICATIONS

Bobbitt, et al., "J. Org. Chem.", vol. 35, No. 4, 1970, pp. 1181–1183.
Woodruff et al., "Peripheral Dopamine Receptors, Proc. of Satellite Symp. of 7th Intl. Congress of Pharmacology", 1978, pp. 57–70.
Costall et al., "J. Pharm. Pharmac", vol. 30, 1978, pp. 514–516.
Woodruff, "Br. J. Clin. Pharm.", Suppl. 2, vol. 4, p. 1055.
Poat et al., "J. Pharm. Pharmac", vol. 30, p. 495.
Freter et al., "J. Hetero. Chem.", vol. 7, 1970, pp. 159–169.

*Primary Examiner*—Donald G. Daus
*Assistant Examiner*—James H. Turnipseed
*Attorney, Agent, or Firm*—William H. Edgerton; Richard D. Foggio; Alan D. Lourie

[57] ABSTRACT

4-Phenyl-1,2,3,4-tetrahydroisoquinolines whose structures have two hydroxy groups substituted at the 3,4-position on the 4-phenyl ring have been found to have renal vasodilating activity upon internal administration. The active ingredients are prepared by cyclizing N-(2-substituted benzyl)-1-(3,4-dimethoxyphenyl)-aminoethanol using either a Lewis acid or an acid cyclizing agent followed by demethylation at the 3,4-dimethoxyphenyl moiety.

19 Claims, No Drawings

RENAL DILATING METHODS AND COMPOSITIONS USING 4-(3,4-DIHYDROXYPHENYL)-1,2,3,4-TETRAHYDROISOQUINOLINES

This invention comprises methods and compositions for improving kidney function in a patient in need of such treatment, for example, by inducing renal vasodilation and decreasing renal vascular resistance which, in turn, increases blood flow in the kidney by using chemical compounds whose structures are characterized by being 8-substituted-4-(3,4-dihydroxy-phenyl)-1,2,3,4-tetrahydroisoquinolines. The active chemical ingredient in which the 8-substituent is an amino is a compound known to the art to have central dopaminergic or antidepressant activities but improvements in kidney function are not reported in the literature for this compound. The compounds having structures in which the 8-substituent is other than amino are new compounds which demonstrate an enhanced renal vasodilation and, especially after oral administration, an improvement in the kidney filtration rate.

DESCRIPTION OF THE PRIOR ART

Prior art publications have described 8-amino-2-methyl-4-(3,4-dihydroxyphenyl)-1,2,3,4-tetrahydroisoquinoline (3,4-dihydroxynomifensine) to have central dopaminergic activity with diminished nomifensine-like activity: B. Costall et al., Communications, J. Pharm. Pharmac., 1978, 30 514; Woodruff, Br. J. Clin. Pharm. Suppl. 2, Vol. 4, page 1055 (1977); J. A. Poat et al, J. Pharm. Pharmac., 1978, 30, 495. Among the generic disclosures in the prior art which may be alleged to include the 8-amino-substituted species or its dimethyl ether are European patent application No. 015; U.S. Pat. No. 3,577,424 or Belgian Pat. No. 698033. None of these references disclose a pharmacodynamic property suggestive of improving kidney function.

Among other generic disclosures are Belgian Pat. No. 844,783 whose disclosed structures have a 7-ether substituent and whose utility is alleged to be anorexic or antidepressant; U.S. Pat. No. 3,872,125 which discloses compounds whose structures have a tertiary alkyl at position 3 and no dihydroxyphenyl substituent along with utility as antidiabetics; and U.S. Pat. No. 3,870,722 which is related to the previous Belgian citation. None of these references disclose the structural features of the active ingredients and resulting renal activity of this invention.

K. Freter et al., J. Heterocycl. Chem. 7 159 (1970) discloses a chemical synthesis of 4-(3,4-dihydroxyphenyl)-2-methyl-1,2,3,4-tetrahydroisoquinoline but no biological utility for the end products. U. M. Bobbitt et. al., J. Org. Chem. 33, 1181, 1970 discloses 4-(3,4-dihydroxyphenyl-7-methoxy-8-hydroxy-1,2,3,4-tetrahydroisoquinoline but again, no biological utility for the end products.

DESCRIPTION OF THE INVENTION

There are two interrelated aspects of this invention. First there are the medical methods and compositions which have been found to improve kidney function by increasing renal vasodilatation. The active ingredients in these new methods and compositions are 4-phenyl-1,2,3,4-tetrahydroisoquinolines whose structures have two hydroxy groups substituted at the 3,4-positions of the 4-phenyl ring. Second there is a subgroup of these active ingredients which are new compounds and which have very potent renal vasodilating activity as well as the property of increasing glomerular filtration rate upon oral administration. The structures of the subgroup of compounds are further characterized by having a non-basic substituent at position 8 of the 1-(3,4-dihydroxyphenyl-1,2,3,4-tetrahydroisoquinoline.

The active ingredients for the pharmacodynamic methods and pharmaceutical compositions of this invention are exemplified by the following structural formula:

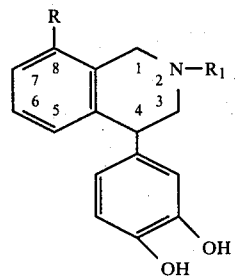

in which R is amino, hydrogen, halo such as chloro bromo, iodo or fluoro, hydroxy or methylthio and $R_1$ is hydrogen or methyl.

The pharmaceutically acceptable acid addition salts having the utility of the free bases of Formula I are particularly useful active ingredients of this invention. They are prepared with both nontoxic inorganic or organic acids, for example: maleic, fumaric, benzoic, ascorbic, succinic, bismethylenesalicylic, methanesulfonic, ethanedisulfonic, acetic, oxalic, propionic, tartaric, salicylic, citric, gluconic, aspartic, stearic, palmitic, itaconic, glycolic, benzenesulfonic, hydrochloric, hydrobromic, sulfuric, cyclohexylsulfamic, phosphoric and nitric acids. The base is reacted with an equivalent or an excess of the chosen acid in an organic solvent. The salt is isolated by filtration or evaporation of the solvent. The hydrohalic and especially methanesulfonic acid salts are preferred. Of course certain of these compounds require two mole equivalents of acid.

Also included in this invention are O-lower alkanoyl esters of the compounds of Formula I, as well as their acid addition salts as described above, having from 2-8 carbon atoms in each alkanoyl group such as acetyl, isobutyryl, propionyl, isovaleryl, n-heptanoyl and others. The ester derivatives are prepared by treating the hydroxy containing parent of Formula I with either a stoichiometric amount or an excess of an acid bromide or anhydride in the presence of an organic base optionally in an organic solvent. If an alkanoyl derivative is desired to be prepared when a secondary nitrogen at position 2 or a primary nitrogen at position 8 is present, these basic centers are protected during O-acylation as known to the art.

The pharmacodynamic methods of this invention comprise administration of an active nontoxic quantity of a compound of Formula I, one of its pharmaceutically acceptable acid addition salts or one of its O-lower alkanoyl esters internally, preferably either orally or parenterally, to a human or animal patient in need of renal vasodilatation. The effect on the kidney is to decrease vascular resistance and increase blood flow. The effect is similar to the renal effects of dopamine and similar clinical effects may be thereby realized such as in treating hypertension or other abnormal cardiovascular conditions. The route of administration may be any that effectively transports the active ingredient to the renal receptors but oral, rectal, intravenous or subcutaneous routes of administration are conveniently used. The compound of Formula I is administered in a nontoxic quantity sufficient to induce renal vasodilatation. Most conveniently the active ingredient is combined with a pharmaceutical carrier and administered to the patient from 1-5 times daily as necessary to effect the desired pharmacodynamic result. The daily dosage is based on total quantities of the base of from about 50 mg to about 1 g per day, administered preferably as 50-350 mg. of base per dosage unit which is administered from 1-5 times daily orally. The parenteral dosage regimen would be lower than the oral regimen. The daily dosage regimen is selected with the conditions known to be factors in the art, for example, the age and weight of the subject, the severity of the clinical disorder, the route of administration and the relative potency of the active ingredient compared to the activity of dopamine in the test systems described hereafter. When the method of this invention is carried out renal vasodilatation similar to that induced by dopamine is realized.

The pharmaceutical compositions of this invention having renal dilating activity of prime use for treating hypotensive patients are prepared in conventional dosage unit forms by incorporating a compound of Formula I, or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 25 mg. to about 500 mg. preferably about 50-350 mg. of active ingredient calculated as the base per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use or syrup, peanut oil, olive oil, water and the like for soft gelatin capsules. Similarly, the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed ranging from rectal suppositories to sterile solutions for parenteral or injectable use. Thus, if a solid carrier for oral administration is used the preparation can be tableted; placed in a hard gelating capsule in powder, regular or sustained release pellet or tablet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The renal dilating activity of the active ingredients of Formula I have been demonstrated by monitoring mean arterial blood pressure (MAP), mean renal blood flow (RBF), renal vascular resistance (RVR) and heart rate (HR) in the normal anesthetized dog by a standard procedure. The compounds are administered as $\mu g/kg/min$ given by cumulative intravenous infusion; each dose was infused for five minutes.

Compound A:
8-amino-4-(3,4-dihydroxyphenyl)-1,2,3,4-tetrahydroisoquinoline hydrobromide:

|  | Dose | % Change in 3 Dogs | | | |
|---|---|---|---|---|---|
|  |  | MAP | RBF | RVR | HR |
| Dopamine | 3 | −3.6 | +23.2* | −22.1* | 0 |
| A | 3 | +1.4 | +4.6 | −2.9 | +4.4 |
|  | 30 | −1.2 | +3.6 | −4.5 | 0 |
|  | 300 | +4.9* | +8.8* | −12.2* | +5.4* |

Compound B:
8-amino-4-(3,4-dihydroxyphenyl)-2-methyl-1,2,3,4-tetrahydroisoquinoline dihydrobromide:

|  | Dose | % Change in 3 Dogs | | | |
|---|---|---|---|---|---|
|  |  | MAP | RBF | RVR | HR |
| Dopamine | 3 | −3.6 | +24.2* | −22.6* | −3.6 |
| B | 3 | −0.3 | +1.9 | −1.7 | 0 |
|  | 30 | +0.8 | +8.8* | −7.1 | +3.0 |
|  | 300 | −0.4 | +17.5* | −13.9* | +17.8* |

In a secondary test for renal vasodilating activity Compound B had an $ED_{15}$ of 0.46 $\mu g/kg$; dopamine 3.5 $\mu g/kg$.

Compound C:
4-(3,4-dihydroxyphenyl)-2-methyl-1,2,3,4-tetrahydroisoquinoline hydrobromide:

|  | Dose | % Change in 2 dogs | | | |
|---|---|---|---|---|---|
|  |  | MAP | RBF | RVR | HR |
| Dopamine | 3 | −14.2* | +27.9* | −32.7* | 0 |
| C | 3 | −2.8 | +8.4* | −9.6* | −7.7* |
|  | 30 | −4.2 | +9.5* | −12.3* | −8.1* |
|  | 300 | −20.8* | −4.6 | −18.2* | +18.7* |

Compound D:
4-(3,4-dihydroxyphenyl)-2-methyl-8-methylthio-1,2,3,4-tetrahydroisoquinoline hydrobromide:

|  | Dose | % Change in 2 Dogs | | | |
|---|---|---|---|---|---|
|  |  | MAP | RBF | RVR | HR |
| Dopamine | 3 | −7.6* | +28.6* | −28.7* | +3.8 |
| D | 3 | −0.7 | +7.2 | −7.3* | −0.6 |
|  | 30 | +0.3 | +12.5* | −11.2* | −1.3 |
|  | 300 | −7.2* | +24.5* | −25.2* | +4.5 |

Compound E:
4-(3,4-dihydroxyphenyl)-8-hydroxy-2-methyl-1,2,3,4-tetrahydroisoquinoline hydrobromide hydrate:

|  | Dose | % Change in 2 Dogs | | | |
|---|---|---|---|---|---|
|  |  | MAP | RBF | RVR | HR |
| Dopamine | 3 | −12.3* | +33.9* | −34.6* | −2.4 |

-continued

|   | Dose | % Change in 2 Dogs ||||
|---|---|---|---|---|---|
|   |   | MAP | RBF | RVR | HR |
| E | 3 | +0.7 | −2.8 | +4.6 | +1.3 |
|   | 30 | −8.6* | +28.3* | −28.4* | +2.0 |
|   | 300 | −17.7* | +14.7* | −28.1 | +10.5* |

Compound F:
8-bromo-4-(3,4-dihydroxyphenyl)-1,2,3,4-tetrahydroisoquinoline hydrobromide:

|   | Dose | % Change in 2 Dogs ||||
|---|---|---|---|---|---|
|   |   | MAP | RBF | RVR | HR |
| Dopamine | 3 | −6.0* | +20.4 | −22.0 | +3.4 |
| F | 3 | −1.8 | −5.5 | +4.3 | −1.3 |
|   | 30 | −0.7 | +8.4* | −8.4 | +3.5 |
|   | 300 | −8.8* | +28.4* | −28.9* | +3.3 |

$ED_{15} = 35$ μg/kg

Compound G:
8-bromo-4-(3,4-dihydroxyphenyl)-2-methyl-1,2,3,4-tetrahydroisoquinoline hydrobromide hydrate.

|   | Dose | % Change in 2 Dogs ||||
|---|---|---|---|---|---|
|   |   | MAP | RBF | RVR | HR |
| Dopamine | 3 | −7.7* | +14.1* | −19.2* | −5.4* |
| G | 3 | −2.0 | +6.0 | −7.3* | 0 |
|   | 30 | 0 | +1.0 | −1.2 | +3.1 |
|   | 300 | −5.1 | +11.7* | −14.6* | +1.3 |

Compound H:
4-(3,4-dihydroxyphenyl)-8-hydroxy-1,2,3,4-tetrahydroisoquinoline hydrobromide hydrate:

|   | Dose | % Change in 3 Dogs ||||
|---|---|---|---|---|---|
|   |   | MAP | RBF | RVR | HR |
| Dopamine | 3 | −4.0 | +30.6* | −25.8* | −2.8 |
| H | 0.3 | −6.3* | +11.6* | −15.9* | −0.8 |
|   | 3 | −9.0* | +1.5 | −9.3* | 0 |
|   | 30 | −22.5* | +6.0* | −24.1* | −0.3 |

Compound I:
8-chloro-4-(3,4-dihydroxyphenyl)-1,2,3,4-tetrahydroisoquinoline hydrochloride:

|   | Dose | % Change in 2 Dogs ||||
|---|---|---|---|---|---|
|   |   | MAP | RBF | RVR | HR |
| Dopamine | 3 | −4.0 | +51.5* | −34.7* | +6.4 |
| I | 3 | 0 | +1.8 | −1.9 | +3.5 |
|   | 30 | −3.0 | +17.4* | −16.7* | +3.5 |
|   | 300 | −12.4* | +33.3* | −33.4* | +17.7* |

The data presented above demonstrates renal vasodilation characterized by increased renal blood flow and decreased renal vascular resistance over a range of from 0.3 to 300 μg/kg/min infusion rates. In general, testing in secondary procedures to obtain an $ED_{15}$ demonstrated a weaker activity than might have been predicted but still a desired profile of pharmacodynamic activity. Also, the methyl ethers of the compounds evaluated in the anesthetized dog procedure in general gave either no or weaker renal vasodilatation.

The criticality of the structures of the active ingredients of Formula I in relation to the pharmacodynamic profile of the compounds is demonstrated by the fact that the following compounds did not show the vasodilating profile in standard screening infusion doses (3–300 μg/kg/min) in the anesthetized dog: 8-amino-4-phenyl-2-methyl-1,2,3,4-tetrahydroisoquinoline maleate (nomifensine), 2-allyl-4,(3,4-dihydroxyphenyl)-8-hydroxy-1,2,3,4-tetrahydroisoquinoline hydrobromide, 4-(3,4-dihydroxyphenyl)-8-hydroxy-2-n-propyl-1,2,3,4-tetrahydroisoquinoline hydrobromide, 8-amino-4-(3-hydroxyphenyl)-2-methyl-1,2,3,4-tetrahydroisoquinoline dihydrobromide or 8-amino-4-(4-hydroxyphenyl)-2-methyl-1,2,3,4-tetrahydroisoquinoline dihydrobromide. These comparative results demonstrate that the 3,4-hydroxyphenyl group is critical and also that substituents at the 2- or N position of the tetrahydroisoquinoline ring must be small such as hydrogen or methyl.

In addition to the therapeutic methods and compositions described above another aspect of this invention is a subgeneric group of new compounds of the formula:

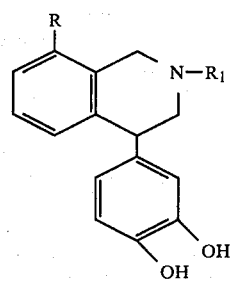

II in which R is halo, hydroxy or methylthio and $R_1$ is hydrogen or methyl together with pharmaceutically acceptable acid addition salts or O-alkanoyl esters thereof.

The new compounds of Formula II have not only a potent vasodilation effect but in contrast with the 8-amino congeners of Formula I also demonstrate a significant increase in the glomerular filtration rate in the phosphate-mannitol renal clearance procedure (V. D. Wiebelhaus et al, Arch. Int. Pharmacodyn. 196 429 (1967).

For example, Compound D in this test procedure demonstrated a significantly increased glomerular filtration rate at 1 mg/kg intravenously; Compound E at 20 mg/kg orally. Compound B had no such activity at 10 and 20 mg/kg orally. This activity combined with the renal vasodilatation described above lead to improved kidney function.

The active ingredients of this invention are prepared by the following reaction sequence:

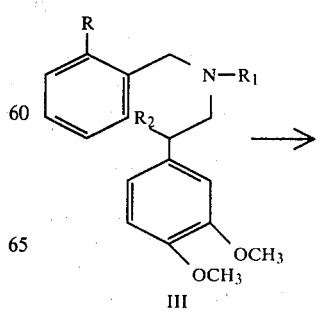

III

-continued

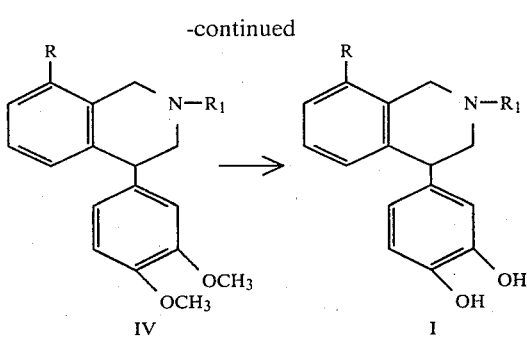

in which R and $R_1$ are defined above. $R_2$ is a substituent which can give rise to a carbonium ion such as hydroxy or a reactive ester thereof.

One method for preparing the starting materials (III) is by condensing an optionally substituted benzylamine with α-bromo-2,3-dimethoxyacetophenone in an organic solvent. The resulting α-benzylamino-3,4-dimethoxy-acetophenone is reduced with a keto reducing agent such as sodium borohydride in a suitable solvent such as alcohol to give the N-benzyl-1-(3,4-dimethoxyphenyl)-2-aminoethanol of Formula III. Another is the Schiff base procedure detailed in the examples.

The intermediate compound is reacted with a cyclizing agent such as a Lewis acid, for example, boron trifluoride, aluminum chloride or stannic chloride in an organic solvent or an acid cyclizing agent as known to the art, for example, polyphosphoric acid, trifluoroacetic acid-sulfuric acid, concentrated sulfuric acid or methane sulfonic acid in methylene chloride. The preferred agent is boron trifluoride or aluminum chloride in a halogenated organic solvent such as chloroform, ethylene trichloride, carbon tetrachloride or methylene chloride with the reaction run at reflux temperature for from 10-24 hours. The resulting ether protected product (IV) is then treated with a demethylating agent such as boron tribromide, hydrogen bromide, aluminum chloride or hydriodic acid to give the desired active ingredient of Formula I.

The following examples are designed to teach the practice of the disclosed invention but not to limit the scope of the invention. All temperatures are on the Centigrade scale.

EXAMPLE 1

A mixture of 7.4 g. (0.044 m) of N-(2-nitrobenzyl)-methylamine, 4.5 g. (0.017 m) of α-bromo-2',3'-dimethoxyacetophenone and 200 ml. of toluene was stirred at room temperature for 24 hours. The mixture was filtered and the filtrate evaporated to give 8.4 g of a yellow oil. The oil was dissolved in 200 ml. of ethanol. About 2 g. of 10% palladium-on-charcoal was added. Hydrogenation was carried out at a low pressure (about 2.58 KPS) of hydrogen for 1½ hours. The mixture was filtered using a filter aid. The cake was washed with chloroform. The combined organic solvent was evaporated to give N-(2-aminobenzyl)-60-methylamino-3',4'-dimethoxyacetophenone, 4.15 g, 78%, m.p. 128°-131°.

Sodium borohydride (0.5 g, 0.013 m) was added portionwise to a mixture of 4.0 g (0.013 m) of the diamine. After stirring for 2 hours, water was added. The methanol was evaporated. The residue was extracted with chloroform to give 3.0 g. (75%) of N-(2-aminobenzyl)-1-(3,4-dimethoxyphenyl)-2-methylaminoethanol as a pale yellow oil.

A mixture of the oil (7.0 g, 0.023 m) in 250 ml of chloroform was added dropwise with stirring to a mixture of 19.7 g (17.0 ml, 0.14 m) of boron trifluoride etherate in 75 ml of chloroform. The mixture was then heated at reflux for 24 hours, cooled and poured into 1 l. of cold water. After neutralization, the phases were separated. The aqueous layer was extracted with chloroform. The chloroform extract was washed with water and dried over sodium sulfate. Evaporation of the solvent gave an oil which solidified after trituration with ether to give 8-amino-4-(3,4-dimethoxyphenyl)-2-methyl-1,2,3,4-tetrahydroisoquinoline; 4.1 g., 60%, m.p. 143°-144°. The base (500 mg.) was reacted with hydrogen chloride in ether to separate the hydrochloride salt, m.p. 219°-221° (d).

A mixture of 3.0 ml (0.033 m) of boron tribromide and 15 ml of methylene chloride was added to a mixture of 1.0 g (0.0033 m) of the dimethoxy base and 30 ml of methylene chloride at −15°. After stirring for ½ hour and then at room temperature for 2½ hours, the mixture was cooled and quenched carefully with methanol. After refluxing and concentration, the quenching process was repeated three times. Evaporation of the solvent gave 8-amino-4-(3,4-dihydroxyphenyl)-2-methyl-1,2,3,4-tetrahydroisoquinoline dihydrobromide [0.92 g, 64%, ml 215-220 (d)].

Anal. calcd. for $C_{16}H_{18}N_2O_2 \cdot 2HBr$: C, 44.47; H, 4.67; N, 6.48. Found: C, 44.95; H, 4.68; N, 6.58.

This material (75 mg of base) is mixed with 300 mg of lactose and 2 mg of magnesium stearate and filled into a hard gelatin capsule which is administered orally to a patient in need of improved renal dilation 3 times daily.

EXAMPLE 2

A mixture of 4.7 g (0.024 m) of 2-amino-1-(3,4-dimethoxyphenyl)ethanol, 3.02 g of 2-nitrobenzaldehyde and 20 ml of methanol was heated on a steam bath until reflux then stirred at room temperature to give a yellow Schiff base (5.6 g, 85%, m.p. 109°-100°. The Schiff base was suspended in 30 ml of methanol then 0.48 g. (0.013 m) of sodium borohydride was added. The solvent was removed in vacuo. The residue was dissolved in a chloroform-water mixture. The phases were separated. The organic portion was washed with water, brine then dried over sodium sulfate. Evaporation of the solvent gave N-(2-nitrobenzyl)-1-(3,4-dimethoxyphenyl)-2-aminoethanol. After recrystallization from ethanol, 5.10 g (90%) of the base was recovered, m.p. 120°-121°.

The base (5.10 g 0.015 m) was reduced by palladium catalyzed hydrogenation as described in Example 1 to give N-(2-aminobenzyl-1-(3,4-dimethoxyphenyl)-2-aminoethanol as a syrup. This material (4.64 g. 0.015 m) in 100 ml of chloroform was added dropwise to 19 ml of boron trifluoride etherate in 125 ml of chloroform at reflux over 2 hours. After heating at reflux for 24 hours, the reaction mixture is mixed with 300 ml of saturated sodium bicarbonate solution slowly. The organic layer was separated, washed with bicarbonate solution, water, brine then dried. Evaporation of the solvent gave a residue which was redissolved in 100 ml of ethanol and 30 ml of ether added. Cooling separated 1.5 g (30%) of 8-amino-4-(3,4-dimethoxyphenyl)-1,2,3,4-tetrahydroisoquinoline, m.p. 131°-133°.

This material (1.8 g, 0.006 m) was demethylated with 6 ml (0.063 m) of boron tribromide as in Example 1 to give 1.6 g of 8-amino-4-(3,4-dihydroxyphenyl)-1,2,3,4-tetrahydroisoquinoline dihydrobromide, m.p. 215°-218°.

This material (150 mg) is mixed with 200 mg of lactose and 2 mg of magnesium stearate then filled into a hard gelatin capsule. These are administered orally 4 times daily to a hypertensive patient.

EXAMPLE 3

Using the experimental procedures of the preceeding examples but starting with 2.72 g (0.02 m) of 2-methoxybenzaldehyde and 4.14 g (0.021 m) of dimethoxynorepinephrine gave 5.25 g (83%) of the Schiff base, m.p. 118°–121°. Reduction of the base with 7.5 g, 0.024 m) sodium borohydride (0.68 g, 0.018 m) gave 6.15 g (81%) of N-(2-methoxybenzyl)-1-(3,4-dimethoxyphenyl-2-aminoethanol, m.p. 100°–103°.

The aminoethanol (1.58 g., 0.005 m) in 40 ml of 1,2-dichloroethane was added to a slurry of 2.8 g (0.02 m) of aluminum chloride in 50 ml. of 1,2-dichloroethane at −20°. The suspension was allowed to warm to 0°, then stirred for 3 hours followed by ½ hour at room temperature. The mixture was poured into cold water. The quench was made basic with 10% sodium hydroxide solution. The organic phase was separated, washed with water, brine and dried over sodium sulfate. Evaporation gave an oil which was purified by chromatography over silica gel to give 0.82 g (55%) of 4-(3,4-dimethoxyphenyl)-8-methoxy-1,2,3,4-tetrahydroisoquinoline, m.p. 106°–112°.

This material (0.80 g., 0.0027 m) was demethylated as described above with 1.5 ml. (0.016 m) of boron tribromide to give 0.16 g (17%) of 4-(3,4-dihydroxyphenyl)-8-hydroxy-1,2,3,4-tetrahydroisoquinoline hydrobromide, m.p. 282°–285° (d).

Anal. calcd. for $C_{15}H_{15}NO_3 \cdot HBr \cdot \frac{1}{2}H_2O$: C, 51.89, H, 4.93; N, 4.06. Found: C, 51.96; H, 4.80; N, 4.24.

This material (175 mg) is encapsulated and given orally 5 times a day to a patient in need of improved kidney function for example a patient with congested heart failure.

EXAMPLE 4

A mixture of 1.85 g. (0.0058 m) of N-(2-methoxybenzyl)-1-(3,4-dimethoxyphenyl)-2-aminoethanol prepared as in Example 3, 4.8 ml of 90% formic acid and 4.5 ml of 37% formaldehyde was heated in a steam bath for 18 hours. The aqueous portion was evaporated and the residue redissolved in water. After making the solution acid with concentrated hydrochloroic acid, the mixture was heated for 20 minutes, cooled, made basic and extracted with chloroform. The organic extract was washed with water, brine then dried. Evaporation gave 1.8 g (93%) of N-(2-methoxybenzyl)-1-(3,4-dimethoxyphenyl)-N-methyl-2-amino ethanol as an oil.

This N-methylaminoethanol (4.5 g., 0.014 m) was cyclized with 9.05 (0.068 m) of aluminum chloride as in Example 3 to give the free base of 4-(3,4-dimethoxyphenyl)-8-methoxy-2-methyl-1,2,3,4-tetrahydroisoquinoline as a foam. The base was converted to the hydrochloride salt, 2.76 g, 56%, m.p. 216°–219°.

The trimethoxy salt (6.44 g, 0.018 m) was demethylated using 10.5 ml (0.11 m) of boron tribromide as described in Example 1 to give 4.2 g (62%) of 4-(3,4-dihydroxyphenyl)-8-hydroxy-2-methyl-1,2,3,4-tetrahydroisoquinoline hydrobromide, m.p. 208°–210°.

Anal. calcd. for $C_{16}H_{17}NO_3 \cdot HBr \cdot \frac{1}{2}H_2O$: C, 53.20; H, 5.30; N, 3.88. Found: C, 53.15; H, 5.16; N, 3.75.

In an alternative sequence the N-methylation using formaldehyde-formic acid is carried out on the 4-(3,4-dimethoxyphenyl)-8-methoxy-1,2,3,4-tetrahydroisoquinoline followed by demethylation using 48% hydrobromic acid at reflux.

This material (100 mg) is encapsulated and given orally 4 times a day to a patient in need of renal vasodilatation.

EXAMPLE 5

Using the Schiff base sequence of Example 2 using 4.2 g (0.03 m) of 2-chlorobenzaldehyde and 6.21 g (0.031 m) of dimethoxynorepinephrine as a starting material gave 8.05 g (84%) of the 2-chloro Schiff base, m.p. 114°–116°. This material (7.8 g, 0.024 m) was reduced with 0.69 g (0.018 m) of sodium borohydride to give 6.25 g. (81%) of N-(2-chlorobenzyl)-1-(3,4-dimethoxyphenyl)-2-aminoethanol, m.p. 89°–91°.

The chloroaminoethanol (3.16 g., 0.01 m) was cyclized using 6.5 g (0.018 m) of aluminum chloride to give the free base of 8-chloro-4-(3,4-dimethoxyphenyl)-1,2,3,4-tetrahydroisoquinoline as an oil. The base was reacted with an excess of hydrogen chloride to give 1.17 g (34.5%) of the hydrochloride salt, m.p. 191°–192°. The salt (1 g., 0.003 m) was demethylated using 4.6 g (0.019 m) of boron tribromide to give 0.91 g (85%) of 8-chloro-4-(3,4-dihydroxyphenyl)-1,2,3,4-tetrahydroisoquinoline hydrobromide, m.p. 278°–282°.

Anal. calcd. for $C_{15}H_{14}ClNO_2 \cdot HBr$: C, 50.52; H, 4.24; N, 3.93. Found: C, 50.42; H, 4.27; N, 3.85.

This material (200 mg) is mixed with 150 mg of lactose and 2 mg of magnesium stearate for filling into a hard gelatin capsule to be given twice daily orally to a hypertensive patient.

EXAMPLE 6

A reaction mixture of 0.96 g (0.003 m) of N-(2-chlorobenzyl)-1-(3,4-dimethoxyphenyl)-2-aminoethanol from Example 5, 3 ml (0.037 m) of formaldehyde and 0.4 g of sodium borohydride in methanol was reacted to give 0.94 g (93%) of N-(2-chlorobenzyl)-1-(3,4-dimethoxyphenyl)-2-methylaminoethanol as an oil. This material (0.6 g., 0.0018 m) and 0.95 g (0.007 m) of aluminum chloride were reacted as described to give 0.42 g (66%) of 8-chloro-4-(3,4-dimethoxyphenyl)-2-methyl-1,2,3,4-tetrahydroisoquinoline hydrochloride, m.p. 212°–217°. This material (0.68 g., 0.002 m) and 1.2 ml (0.013 m) of boron tribromide were reacted to give 0.70 g. (94%) of 8-chloro-4-(3,4-dihydroxyphenyl)-2-methyl-1,2,3,4-tetrahydroisoquinoline hydrobromide, m.p. 266°–269°.

Anal. calcd. for $C_{16}H_{16}ClNO_2 \cdot HBr \cdot \frac{1}{2}H_2O$: C, 50.61; H, 4.71; N, 3.69. Found: C, 50.83; H, 4.64; N, 3.81.

EXAMPLE 7

Repeating the reaction sequence in Example 5 but starting with 2-bromobenzaldehyde in place of 2-chlorobenzaldehyde gave 8-bromo-4-(3,4-dihydroxyphenyl)-1,2,3,4-tetrahydroisoquinoline hydrobromide, m.p. 273°–277°.

Anal. calcd. for $C_{15}H_{14}BrNO_2 \cdot HBr$: C, 44.92; H, 3.77; N, 3.49. Found: C, 45.17; H, 3.85; N, 3.37.

EXAMPLE 8

A mixture of 5.5 g. (0.015 m) of N-(2-bromobenzyl)-1-(3,4-dimethoxyphenyl)-2-aminoethanol from Example 7, 2.15 g (0.045 m) of 88% formic acid and 3.06 g (0.038 m) of 37% aqueous formaldehyde was reacted to give 3.8 g (66%) of the N-methylethanolamine as an oil. This material (3.75 g, 0.01 m) was reacted with 6.5 g (0.5 m) of aluminum chloride in methylene chloride. The free base isolated from the ring closure was reacted with hydrogen chloride in dry methylene chloride to give 2.63 g (67%) of 8-bromo-4-(3,4-dimethoxyphenyl)-2-methyl-1,2,3,4-tetrahydro-isoquinoline hydrochloride m.p. 233°–236° (d). This product (0.75 g., 0.002 m) is treated with 1.12 ml (0.02 m) of boron tribromide to give 0.66 g (85%) of 8-bromo-4-(3,4-dihydroxyphenyl)-2-methyl-1,2,3,4-tetrahydroisoquinoline hydrobromide, m.p. 271°–276°.

Anal. calcd. for $C_{16}H_{16}BrNO_2 \cdot HBr \cdot \frac{3}{4}H_2O$: C, 44.83; H, 4.35; N, 3.27. Found: C, 44.97; H, 4.10; N, 3.05.

This material (250 mg) is encapsulated and given 4 times orally to a patient in need of improvement in kidney function.

EXAMPLE 9

A solution of 3.53 g (0.0097 m) of 8-bromo-4-(3,4-dimethoxyphenyl)-2-methyl-1,2,3,4-tetrahydroisoquinoline from Example 7 in 50 ml. of toluene was added slowly to a stirred solution of 15.6 ml (0.039 m) of 2.5 m butyl lithium in n-hexane dissolved in 50 ml of toluene cooled to −50° and under nitrogen. After stirring for 15 minutes, 5.0 ml (0.055 m) of methyl disulfide in 25 ml of toluene was added. The mixture was steamed for one hour allowing this temperature to rise then poured into 300 ml of water. The mixture was made acidic with 10% hydrochloric acid. The phases were separated. The aqueous layer was washed with ether, made basic and extracted with ether. After washing with water and brine then drying over sodium sulfate, the ether extract was evaporated to give a crude oil which was passed over a silica gel column to give 2.0 g (68%) of the oily base. This was reacted with hydrogen chloride in ether to give the hydrochloride salt (90%, m.p. 200°–212°) of 8-methylthio-4-(3,4-dimethoxyphenyl)-2-methyl-1,2,3,4-tetrahydroisoquinoline.

This product (1.45 g., 0.004 m) was reacted with 2.7 ml (0.024 m) of boron tribromide as described to give 1.1 g (72%) of 8-methylthio-4-(3,4-dihydroxyphenyl)-2-methyl-1,2,3,4-tetrahydroisoquinoline hydrobromide, m.p. 248°–252°.

Anal. Calcd. for $C_{17}H_{19}NO_2S \cdot HBr$: C, 53.41; H, 5.27; H, 3.66. Found: C, 53.59; H, 5.20; N, 3.65.

The hydrobromide salt (500 mg) is neutralized in a bicarbonate/ether mixture. One half of the ether layer containing the base is then treated with a slight excess of methane sulfonic acid to give 85 mg. of the methanesulfonic acid salt of the 8-methylthio-4-(3,4-dihydroxyphenyl)-2-methyl-1,2,3,4-tetrahydroisoquinoline. The other aliquot is evaporated to give the base.

The salt product is filled into hard gelatin capsules at the rate of 150 mg (base) per capsule and given 5 times daily to a patient in need of improved kidney function.

In similar fashion the hydrochloride, hydrobromide, sulfate or phosphate salts are prepared.

EXAMPLE 10

A mixture of 1.0 g of 8-hydroxy-1-(3,4-dihydroxyphenyl)-2-methyl-1,2,3,4-tetrahydroisoquinoline hydrobromide prepared as in Example 4 above and 200 ml of trifluoroacetic acid is mixed with 1.3 ml of acetyl bromide. After heating at reflux for 2 hours, the mixture is evaporated to dryness. The residue is purified by recrystallization to give 8-acetoxy-1-(3,4-diacetoxyphenyl)-2-methyl-1,2,3,4-tetrahydroisoquinoline hydrobromide. Similarly isobutyryloxy, propionyloxy, isovaleryloxy, n-butylryloxy and n-heptanoyloxy derivatives are prepared.

As a N-protecting group benzyl is useful since it can be prepared by reaction with benzylbromidetriethylamine. Then the O-acylation is run and the N-benzyl group removed by catalytic hydrogenation in the presence of a palladium catalyst.

What is claimed is:

1. A method of producing renal vasodilation in a patient in need thereof comprising administering to said patient internally an effective nontoxic quantity selected from the range of 50 mg to 1 g of a compound of the formula:

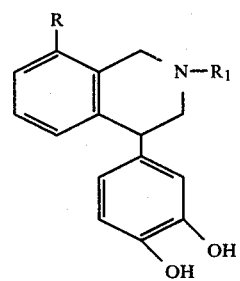

in which R is hydroxy, hydrogen, halo or methylthio and $R_1$ is hydrogen or methyl, one of its O-lower alkanoyl esters, or one of its pharmaceutically acceptable acid addition salts.

2. The method of claim 1 in which the quantity of the compound is from 50–350 mg. and is administered orally from 1 to 5 times daily.

3. The method of claims 1 or 2 in which R is halo, hydroxy, or methylthio.

4. The method of claims 1 or 2 in which R is methylthio.

5. The method of claims 1 or 2 in which the compound is of the formula:

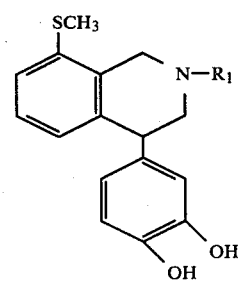

in which $R_1$ is hydrogen or methyl as a pharmaceutically acceptable acid addition salt.

6. The method of claims 1 or 2 in which the compound is 8-methylthio-4-(3,4-dihydroxyphenyl)-2-methyl-1,2,3,4-tetrahydroisoquinoline or one of its pharmaceutically acceptable acid addition salts.

7. A pharmaceutical composition in dosage unit form having renal dilating activity comprising a quantity of a compound selected from the range of 40–350 mg and which is nontoxic and renal dilating said compound being of the structure:

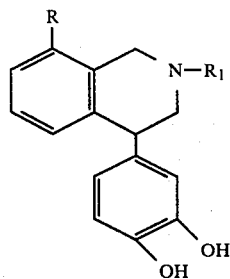

in which R is hydroxy, hydrogen, halo or methylthio and $R_1$ is hydrogen or methyl, one of its O-lower alkanoyl esters, or one of its pharmaceutically acceptable acid addition salts combined with a pharmaceutical carrier.

8. The composition of claims 7 in which R is hydroxy, halo or methylthio.

9. The composition of claims 7 in which R is methylthio.

10. The composition of claims 7 in which R is methylthio and $R_1$ is methyl, the composition is for oral or parenteral use and the compound is in the form of a pharmaceutically acceptable acid addition salt.

11. A compound of the structure:

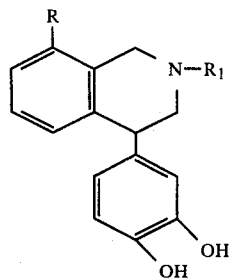

in which R is halo, hydroxy or methylthio and $R_1$ is hydrogen or methyl, one of its O-lower alkanoyl esters, or one of its pharmaceutically acceptable acid addition salts.

12. The compound of claim 11 being 8-methylthio-4-(3,4-dihydroxyphenyl)-2-methyl-1,2,3,4-tetrahydroisoquinoline or one of its pharmaceutically acceptable acid addition salts.

13. The compound of claim 11 being 8-methylthio-4-(3,4-dihydroxyphenyl)-2-methyl-1,2,3,4-tetrahydroisoquinoline.

14. The compound of claim 11 being 8-methylthio-4-(3,4-dihydroxymethyl)-2-methyl-1,2,3,4-tetrahydroisoquinoline methane sulfonic acid salt.

15. The compound of claim 11 being 8-chloro-4-(3,4-dihydroxyphenyl)-1,2,3,4-tetrahydroisoquinoline or one of its pharmaceutically acceptable acid addition salts.

16. The compound of claim 11 being 8-hydroxy-4-(3,4-dihydroxyphenyl)-1,2,3,4-tetrahydroisoquinoline or one of its pharmaceutically acceptable salts.

17. The compound of claim 11 in which R is halo.

18. The compound of claim 11 being 8-bromo-4-(3,4-dihydroxyphenyl)-1,2,3,4-tetrahydroisoquinoline or one of its pharmaceutically acceptable salts.

19. The compound of claim 11 in which R is hydroxy.

* * * * *